United States Patent [19]

Mori et al.

[11] 4,370,300

[45] Jan. 25, 1983

[54] AROMATIC ODORANT EMITTING DEVICE

[75] Inventors: Yasuyuki Mori; Haruo Nishimura, both of Osaka; Yoshikazu Sugahara, Fujiidera, all of Japan

[73] Assignee: Duskin Franchise Kabushiki Kaisha, Osaka, Japan

[21] Appl. No.: 324,487

[22] Filed: Nov. 24, 1981

[30] Foreign Application Priority Data

Jan. 23, 1981 [JP] Japan .................... 56-8105[U]
Jun. 10, 1981 [JP] Japan .................... 56-85463[U]

[51] Int. Cl.³ .................... B01F 3/04; A61L 9/04
[52] U.S. Cl. .................... 422/108; 422/105; 422/110; 422/124; 261/96; 261/102; 261/DIG. 17
[58] Field of Search .................... 422/105, 108, 110, 124; 261/DIG. 17, 96, 102

[56] References Cited

U.S. PATENT DOCUMENTS

| | | | |
|---|---|---|---|
| 2,612,432 | 9/1952 | Boddy | 422/105 X |
| 2,814,081 | 11/1957 | Stevenson | 422/105 X |
| 3,796,541 | 3/1974 | Gentil | 422/108 |
| 3,872,280 | 3/1980 | Dalen | 422/124 X |
| 4,166,087 | 8/1979 | Cline et al. | 261/96 |
| 4,294,778 | 10/1981 | DeLuca | 422/124 X |
| 4,301,095 | 11/1981 | Mettler et al. | 422/124 X |

FOREIGN PATENT DOCUMENTS

2061546 3/1969 France .................... 422/124

Primary Examiner—Arthur D. Kellogg
Attorney, Agent, or Firm—Cushman, Darby & Cushman

[57] ABSTRACT

An aromatic odorant emitting device comprising a mainbody case and a cover case, said device including an odorant, and an evaporator immersed with the aromatic odorant, and a fan unit which blows the air to the evaporator so as to control the evaporation rate of the odorant in response to the temperature and the illumination intensity in the room, with the aid of a thermosensor and a photosensor, so that a constant aromatic odorant evaporation is provided.

8 Claims, 22 Drawing Figures

AROMATIC ODORANT EMITTING DEVICE

BACKGROUND OF THE INVENTION

1. Field of the Invention

This invention relates to an aromatic odorant emitting device, and more particularly, an aromatic odorant emitting container including a liquid aromatic odorant, an evaporating device arranged at a lower portion of said container immersed with said odorant by the aid of capillary phenomenon, a fan rotating with a battery above said evaporator, in opposite relationship. The rotational speed of said fan can be variably controlled with temperature and illumination intensity in a room in order to suppress the evaporation of the aromatic odorant when the temperature and illumination in a room are high and to expedite the evaporation of the odorant when the temperature and illumination are low, so that a generally constant amount of the aromatic odorant can be emitted in response to the temperature and illumination intensity in the room.

2. Description of the Prior Art

Conventional aromatic odorant emitting devices located in a closet such as a washing room have been merely hung on a wall of the room, and the odorant emitting container has contained the odorant which has only continued to emit the odor until the odorant has been exhausted. There have been no odorant emitter controlling the evaporation rate in response to the change of the temperature and the illumination in the room so that the aromatic odorant has always emitted at a constant rate.

Further aromatic odorant emitting device has been known. This device has been employing an aromatic odorant absorbing piece which absorbs the liquid aromatic odorant by the aid of the capillary action for immersing therein and which has naturally emitted the odorant from its evaporating surface without employing any artificial compulsory emitting means. However, such emitting device with the utilization of the natural evaporation caused mainly by a temperature difference, has not been expected to permit a comfortable emission effect.

In order to overcome such drawbacks, there has been developed an aromatic emitting device which has expedited the aromatic odorant emission with fan blades, which are rotated with an electric motor driven by a battery and have forcibly blown an air to the evaporation surface of the odorant absorbing piece. This device has given an enough emission effect, but it has raised many problems, because the motor is driven at a constant revolution speed throughout a day and hence a year.

The first problem is the room temperature fluctuation based on the seasonal (annual) variation. Since the aromatic odorant shows a higher emission rate as the room temperature rises, one should suppress the fan speed in summer while raise the fan speed in winter. The above compulsory emitting device having no such function, has had an extremely high aromatic odorant emitting effect in summer while the low effect in winter, so that the constant comfortable odorant emitting effect has not been expected.

The second problem is that the bright-dark fluctuation as the short periodic (daily) fluctuation is disregarded. Since no person ought to normally be in the room when the room is dark in the night and even the day time, the high speed fan rotation is meaningless because of the uneconomical waste of the odorant. To neglect the countermeasure against the bright-dark fluctuation is an essentially important drawback rather than neglecting the countermeasure against the temperature fluctuation.

SUMMARY OF THE INVENTION

To overcome such drawbacks in the prior art, this invention concerns an aromatic odorant emitting device consisting of an aromatic odorant emitting container including a liquid aromatic odorant, an evaporating device arranged at a lower portion thereof, immersed with said odorant by the aid of the capillary phenomenon, a fan rotating with a battery above said evaporating device. The rotational speed of said fan can be variably controlled with the temperature and the illumination intensity in a room so as to suppress the evaporation of the aromatic odorant when the temperature and the illumination in the room are high and so as to expedite the evaporation of the odorant when the temperature and the illumination are low. Therefore, the primary object of the present invention is to provide an aromatic odorant emitting device which can automatically control and minimize the emitted volume of the aromatic odorant in response to changes of the temperature and the illumination in the room.

Another object of the present invention is to provide an aromatic odorant emitting device whose liquid aromatic odorant can be easily replaced.

A further object of the present invention is to provide an aromatic odorant emitting device whose construction is simple and which can be easily assembled.

A still further object of the present invention is to provide an aromatic odorant emitting device comprising essentially instruments and circuits which electrically and/or electronically drive and control said device emitting the aromatic odorant.

DESCRIPTION OF THE PREFERRED EMBODIMENTS

The preferred embodiment of this invention will be hereinafter discussed in detail with reference to the accompanying drawings.

The figures show an aromatic odorant emitting container 1 comprising a mainbody case 2 and a cover case 3.

Figures 6, 7:
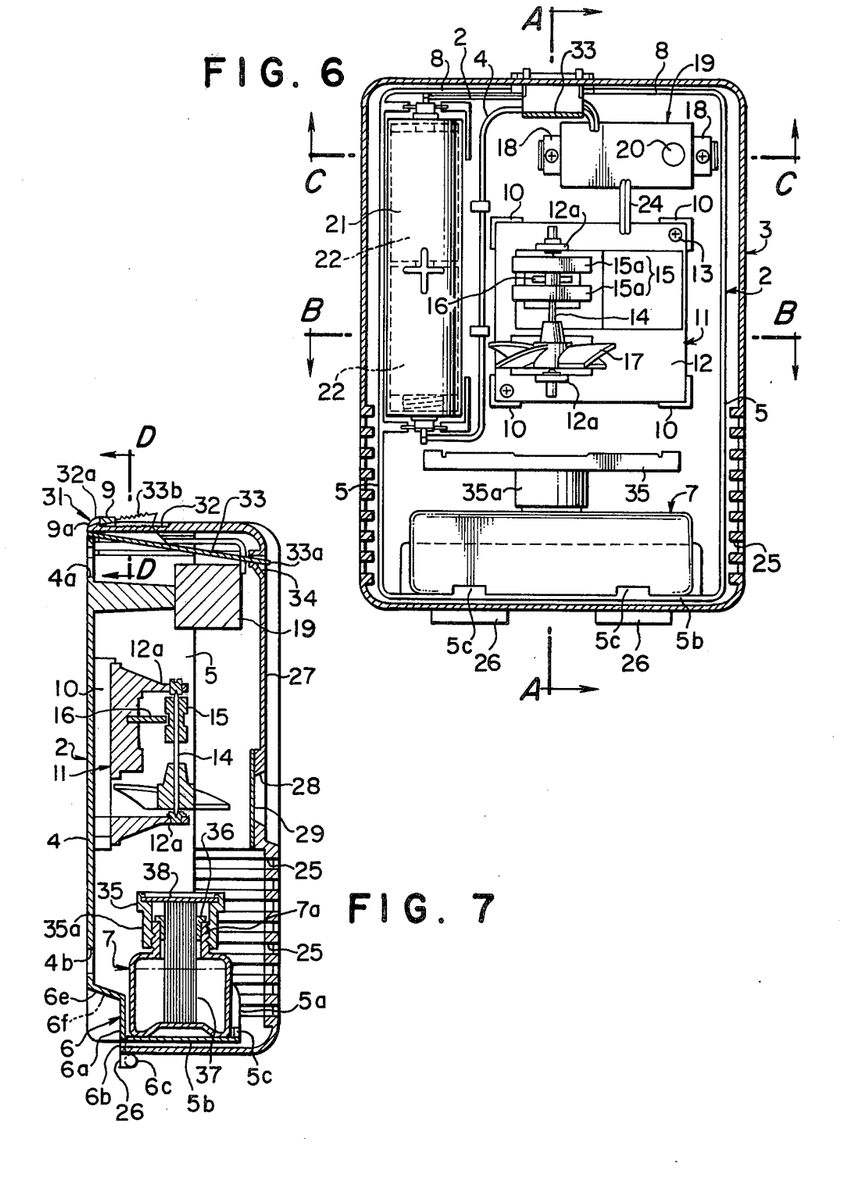
FIG. 6 is a front elevational cross section.
FIG. 7 is a cross section along line A—A in FIG. 6.
Figure 8:
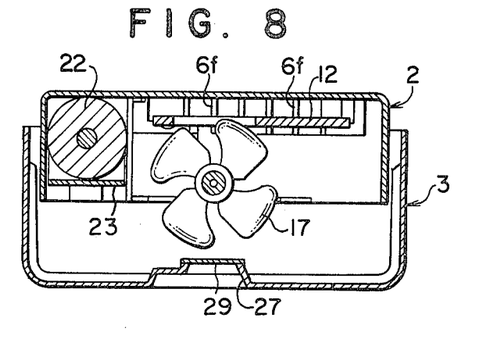
FIG. 8 is a cross section along line B—B in FIG. 6.
Figure 9:
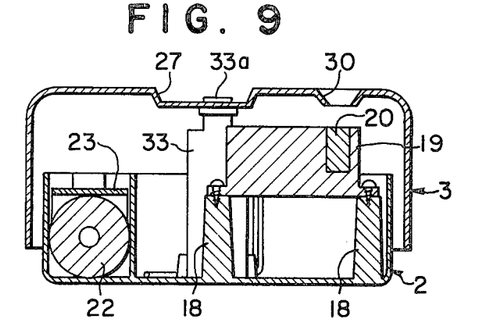
FIG. 9 is a cross section along line C—C in FIG. 6.

As apparently shown in FIG. 6, the mainbody case 2 is formed in a box shape slightly smaller than the cover case 3 and through bores 4a, 4b are provided on the upper and lower positions of the rear face 4 of the case 2, for attaching the container 1 onto a wall along an axial line.

Figure 1:
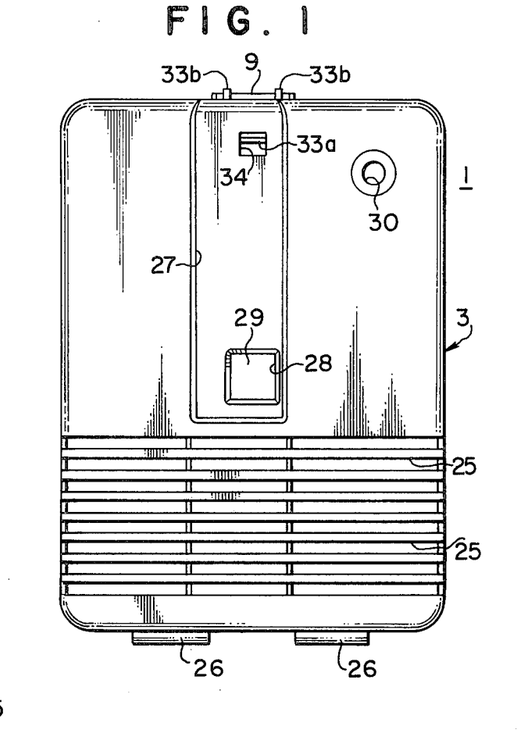
FIG. 1 is a front elevational view.
Figure 2:
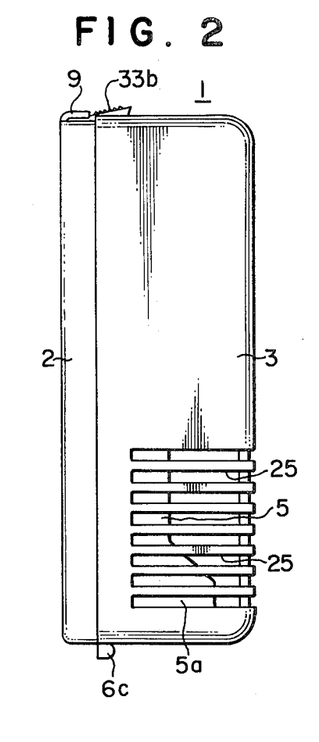
FIG. 2 is a side elevational view.
Figure 3:
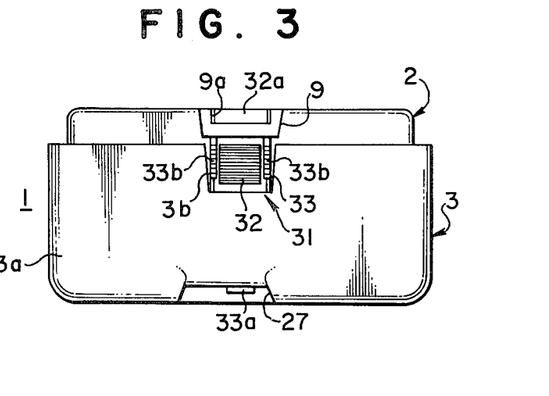
FIG. 3 is a top plan view.
Figure 4:
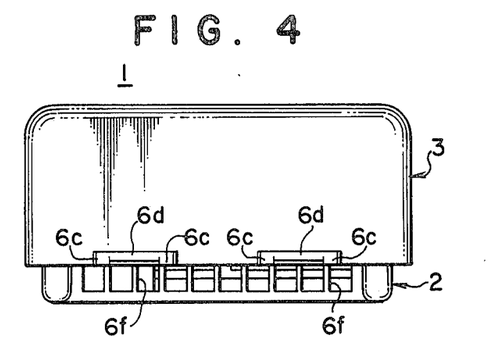
FIG. 4 is a bottom plan view.
Figure 5:
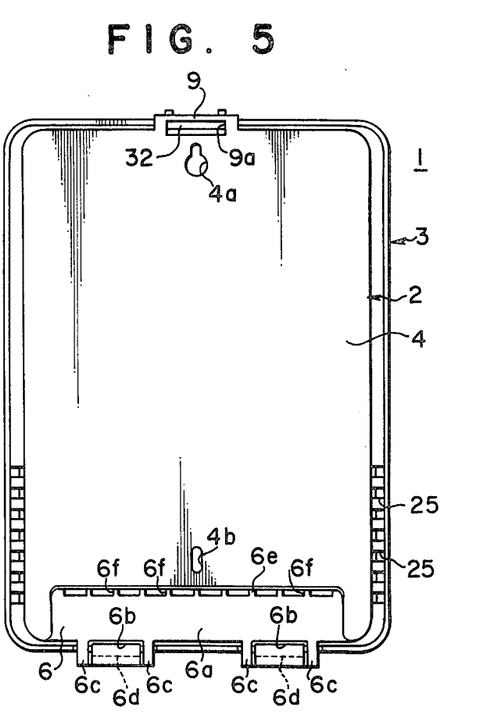
FIG. 5 is a rear elevational view.

Extending forwardly from both sides of the rear wall 4 are left and right side walls 5, at the lowest ends of which are formed projection members 5a, 5a, and these members are linked with a bottom plate 5b. As shown in FIG. 7, an inwardly retreating portion 6 is formed at a corner of the lower portion of the rear wall of the mainbody case 2 formed with the lower portion of said rear wall 4 and the bottom plate 5b. Formed at the lower portions of both sides of an upright wall 6a of said retreated portion 6 are square openings 6b and a pair of supporting frame 6c, 6c are extending downwardly from said upright wall 6a sandwiching said opening 6b, as illustrated in FIG. 5. These supporting frames 6c, 6c extend further inwardly beyond the openings 6b, and a horizontal bridge frame 6d is bridged between the lower ends of said frames 6c, 6c. An upper wall 6e of the retreating wall is formed gradually inclining toward the upright wall 6a, and a plurality of opening 6f are formed with a certain spaced distance, as shown in FIG. 5.

Furthermore, projections 5c with a low height, extending uprightly above at positions generally in spaced opposite with said opening 6b, near the both ends of a front rim of said bottom plate 5b are provided, and contained among these projections 5c, 5c and the upright wall 6a is an aromatic odorant container 7 filled with an aromatic odorant, which will be discussed in detail later.

On the other hand, integrally formed at the upper portions of the both side plates 5, 5 of the mainbody case 2 are top plates 8, 8 which extend along an upper end rim of the rear wall 4 toward near the center of the upper end rim. Formed at corresponding portions between these top plates 8, 8 is an L-shaped engagement piece 9 forwardly from the upper end rim of the rear wall 4 with a one stage higher level than the top plates 8, 8, and an opening 9a is formed at a corner of said piece 9 and thus said piece 9 is in a form of a frame member.

As shown in FIGS. 6 and 7, square projections 10 are provided at positions corresponding to each corner of a square member on the side face of the rear wall in opposite to the cover case 3 and with the aid of these projections a base 12 of the fan unit 11 is fixed with screws 13.

The fan unit 11 is integrally formed so that its control circuit portion can be fully sealed with an alloy such as aluminum and other equivalents, and integrally protruded from a part of the unit are supporting frames 12a, 12a at each corresponding portion above and below the unit 11. A rotary axis is rotatably received between the supporting frames 12a, 12a and at a top of the rotary axis 14 is fixed a rotor 15 comprising a pair of rectangular frame members 15a, 15a.

A permanent magnet (not shown) is contained at each end of said frame members 15a, 15a, in opposite of which is a coil 16 provided on the base 12 as shown in FIG. 7.

A fan 17 is fixed at a lower end of the rotary axis 14.

On the other hand, protruded from the rear wall 4 at the upper portion of the fan unit 11 toward the cover case 3 is a pair of supporting pillars 18 as shown in FIG. 6, at each tip end of which is provided a thermosensor 18. A photosensor 20 such as CdS forms a part of the thermosensor 19, and the illumination intensity (in Lux unit) and the temperature detected with these photosensor 20 and the thermosensors 19 are transduced to voltage values. These voltages are applied via a lead wire 24 to the control circuit of said fan unit 11 which in turn controls current supplied to a coil 16, and the rotation of the fan 17. More in detail, for example, in a case of the room temperature below 15° C. and the illumination above 5 Lux, the fan 17 is controlled to rotate at 850 r.p.m., and in a case of the room temperature above 15° C. and the illumination above 5 Lux, the fan rotates at 650 r.p.m., and in other case of the illumination below 5 Lux in spite of the temperature, the fan is controlled to rotate at 450 r.p.m. Provided at a portion of the mainbody case near the left side where the fan unit 11 is positioned, is a battery box 21 containing a battery 22, as shown in FIG. 6. This battery box 21 has a detachable cover 23, so that a replacement or exchange of the battery can be easily done. This battery box 21, said thermosensor 19, the photosensor 20 and the fan unit 11 are connected with a lead wire 24 and the battery supplies its power to the latter three members.

On the other hand, the cover case 3 is formed a little larger than said mainbody case 2 in a box shape, and a plurality of through slits 25 are formed at both side ends and the front of the lower portion of said case 3. Through the slits 25 the aromatic odor is compulsorily emitted as discussed later in detail.

At a lower end opening rim, engagement pieces 26 with a L-shaped cross section bending downwardly are provided at positions corresponding to the positions between the supporting frames 6c, 6c. These engagement pieces 26 are inserted into the rectangular openings 6b between the supporting frames 6c, 6c and these are rotatably attached on the mainbody case 2 by engaging these tip ends with the horizontal frames 6d bridged between said frames 6c, 6c.

Provided near a center portion of the front face of the cover case 3 is a rectangular concave 27 extending toward the upper rim of the cover case 3 at an upper end of said slits 25, and a quadrilateral opening 28 is formed at a lower end of the concave 27 corresponding to said fan 17. The inner side of the opening 28 is closed with a sticked transparent plate 29 in order that one may see its inner side but may not insert his or her fingers, as shown in FIG. 7. This opening 28 is an window for watching or supervising the rotational condition of the fan 17.

Near the right shoulder of the cover case 3 when viewed in front, a conical opening 30 is formed in opposite to said photosensor 20 which detects the illumination intensity in the room.

On the other hand, provided at a top end of the cover case 3 is a locking mechanism 31 which comprises a washboard-like piece 32 integral with the top plate 3a and a slide lever 33.

Figure 13:
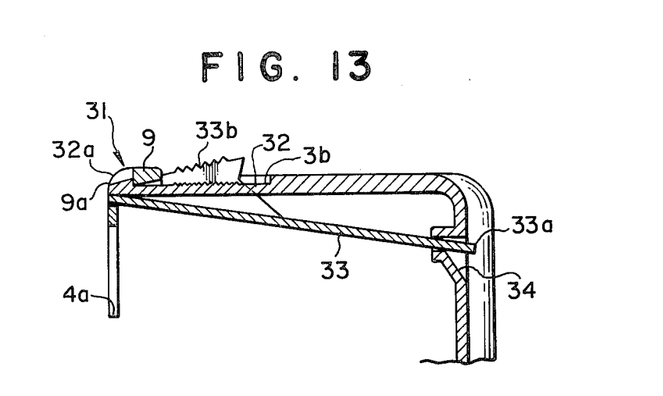
FIG. 13 is a partial enlarged scale view in FIG. 7.
Figure 14:
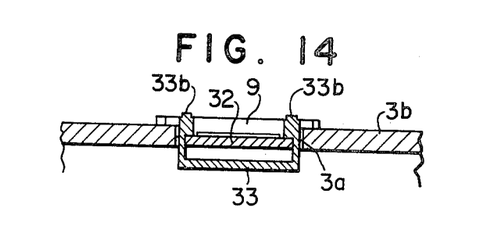
FIG. 14 is a cross section along line D—D in FIG. 7.

As clearly shown in FIGS. 7, 13 and 14, the washboard-like piece 32 is protruded toward the mainbody case 2 in a lower place by a thickness of the top plate 3a and integral with said top plate 3a. Its tip end is extended to a position engageable with the engagement piece 9 formed on the mainbody case 2, and its tip end has at its upper side a hook 32a, which is inserted into the opening 9a of the engagement piece 9 and hooked therein. As the washboard-like piece 32 is shaped to face within the square notch 3b formed toward the opening of the top plate 3a, its root end is integral with the cover case 3 but has a free tip end hence it can elastically deform if one pushes thereon.

Figures 15, 16:
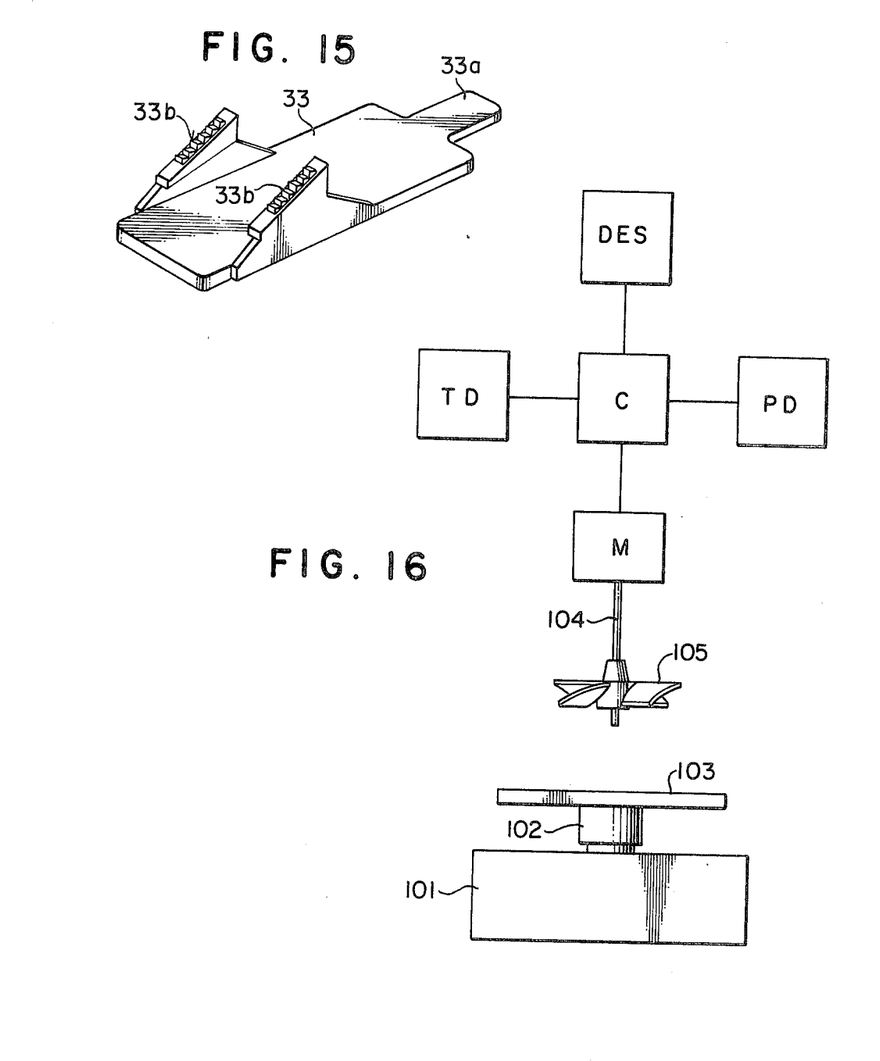
FIG. 15 is a perspective view of a slide lever.
FIG. 16 is an explanatory view of the aromatic odorant device of this invention.

The slide lever 33 takes a position at the lower side of the washboard-like piece 32 and its thinning one end 33a extends from the opening 34 formed near the upper end of the concave 27 of the cover case 3 toward a front of the cover case and inclines toward the washboard-like piece 32 side as shown in FIGS. 13 through 15. A pair of holding pieces 33b are provided at the both side rims of its inner side end sandwiching both sides of said washboard-like piece 32. These holding pieces 33b extend upwardly from a space between the washboard-like piece 32 and the notch 3b and its upper ends reach the upper ends of the both side rims of the washboard-like piece 32 and they are slidably formed in a state holding the washboard-like piece 32. The holding pieces 33b have at those upper ends saw-like wave concaves and convexes for an easy operation. The holding pieces 33b are restricted so as to move between the root sides of the notch 3b and the hook 32a. Since the locking mechanism 31 has the construction mentioned above, the piece 32 can be perfectly locked to the main body case 2 as follows: after the engagement pieces 26 of the lower portion of the cover case 3 have been engaged with the horizontal frames 6d at the lower end of the mainbody case 2, the cover case 3 is rotated around the engaged portions to be mated with the case 2, so that the case 3 cover the mainbody case 2. Then, by inserting the washboard-like piece 32 into the opening 9a of the engagement piece 9 of the mainbody case 2 and elastically deforming the piece 32, the hook 32a is hooked with the engagement piece 9 through the opening 9a. Finally, by pushing one end 33a of the slide lever 33, the slide lever 33 advances and its forward tip end is mated into the opening 9a of the engagement piece 9. Consequently, since the washboard-like piece 32 is pressed upwardly by the forward tip end of the slide lever 33, the piece 32 can be perfectly locked to the mainbody case 2.

When releasing the locking, pulling the holding member 32 with a finger causes the tip end of the slide lever 33 to retreat from the opening 9a of the engagement piece 9, so that the washboard-like piece 32 becomes elastically deformable. Then, by pushing downwardly the washboard-like piece 32, the hook 32a comes off from the engagement piece 9 and thus, the cover 3 can be dismantled.

Figure 10:
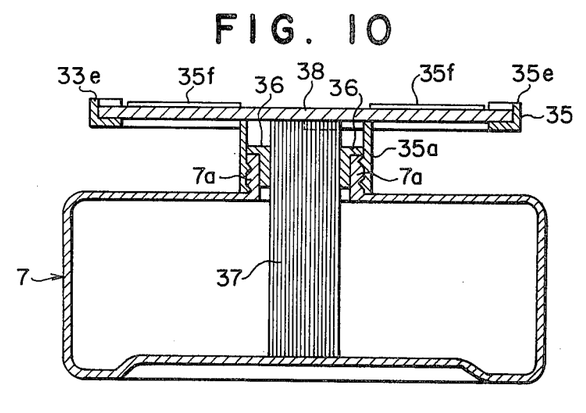
FIG. 10 is a front elevational cross section of the container.

On the other hand, the aromatic odorant container is, as shown in FIG. 10, a square box with the width which is insertable between the bottom plate 5b of the mainbody case 2 and the upright wall 6a, as shown in FIG. 7, and the length which extends near the right and left side ends of the bottom plate 5b.

A predetermined amount of the liquid aromatic odorant is filled in this container 7.

Formed at a center of the upper end of the odorant container 7 is openings 7a with threads on its periphery on which is spirally mated a cylindrical member 35a formed at a lower end of the evaporator 35.

Fixed within said openings 7a through a packing 36 is a thin bundle 37 of glass fibers, a lower end of which extends near to the bottom of the aromatic odorant container 7.

Figure 11:
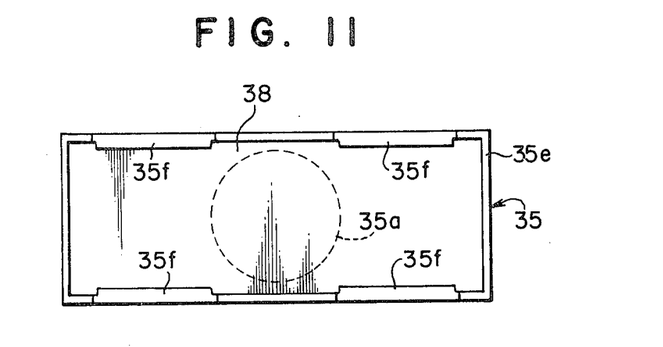
FIGS. 11 and 12 are a plan view and a bottom view of the evaporator, respectively.
Figure 12:
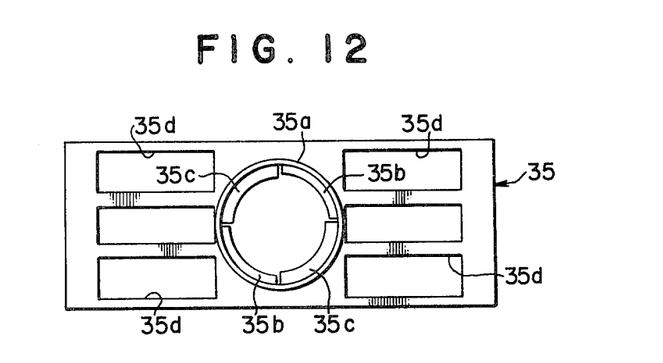

The evaporator 35 is formed in rectangular shape as shown in FIGS. 11 and 12, and formed at its lower surface of the center portion is a cylindrical member 35a, opposite with inner periphery of which are formed arcuate projections 35b at each different height, which are spirally mated with threads formed on the opening 7a. On the upper end are shaped arcuate projections 35c to be stoppers. A plurality of openings 35d are formed on the evaporator 35, sandwiching said cylinder member 35a from right and left sides, as shown in FIG. 12. The upper periphery of the evaporator 35 is surrounded with side walls 35e, on longer sides of which are provided projections 35f in opposed relation. An absorbing piece 38 comprising, for example, nonwoven cloth is located between this projection 35f and an upper face of the evaporator 35. This absorbing piece 38 is confronted with an opening on the upper end of the cylindrical member 35a, and abuts on the upper end of the glass fiber bundle 37, as shown in FIG. 7. Hence, the liquid aromatic odorant contained within the odorant container 7 is absorbed by the capillary action of the glass fibers 37 in a state that the evaporator 35 is attached therewith. Accordingly, the absorbing piece 38 is always immersed with the liquid aromatic odorant, since the liquid aromatic odorant is always supplied to the absorbing piece.

Now, an operation of this embodiment constructed above will be discussed.

First, the cover case 3 is opened, fixing the mainbody case 2 on the wall, etc., and the aromatic odorant container 7 filled with the liquid aromatic odorant is placed on the bottom plate 5b and the evaporator 35 is set in oppose to the fan 17. Hence, mounting the battery 22 within the battery case 21, it supplies the electric current through the lead wire 24 to the thermosensor 19, the photosensor 20 and the fan unit 11, so that the fan starts to rotate. Mounting the cover case 3 onto the mainbody case 2, the fan 17 blows an air to the absorbing piece 38 and the aromatic odorant immersed therein is forcibly evaporated and emitted into the room through the slits 25.

When the aromatic odorant has been emitted with the air, the necessary air is then absorbed into an interior of the case through the relatively large gap between the mainbody case 2 and the cover case 3, and through slits 6f provided at the lower portion of the rear side of the mainbody case 2.

The temperature and the illumination intensity in the room are always detected through an opening 30 formed on the cover case 3 by means of the thermosensor 19 and the photosensor 20. The detected temperature and illumination are transduced to the electric signals, which are then supplied through the control circuit (not shown) to the fan unit 11. When the room temperature is lower than 15° C. and the room illumination is brighter than 5 Lux, the fan is controlled to rotate about 850 r.p.m., and the emission volume of the odorant is compulsorily expedited. When the room temperature is higher than 15° C. and the illumination is higher than 5 Lux, the fan 17 is limited so as to rotate about 650 r.p.m. and controlled so as to make the emission rate constant, since the natural emission rate of the odorant is larger than the lower temperature state. Regardless the temperature, when the illumination intensity is lower than 5 Lux (the environment is dark and few persons come in and come out), the fan 17 is limited to minimize the rotation at a state lower than 450 r.p.m., in order to suppress the emission rate of the odorant to the minimum.

As recognized apparently from the aforegoing explanation, since the odorant emitting device based on the main embodiment of this invention comprises an open and close-free mainbody and a cover case, a replacement of the liquid odorant can be easily done. Moreover, as said odorant emitting device includes a thermosensor and a photosensor, the rotational speed of the fan is lowered in response to the dark illumination in the room so as to suppress the evaporation rate of the odorant, and the rotational speed of the fan is increased so as to expedite the emission rate of the odorant in response to the bright illumination. The rotational speed of the fan is also regulated with the temperature in the room similar to the illumination and can be automatically controlled so as to make the evaporation rate of the odorant almost constant, so that it does not give an unfavorable feeling. Furthermore, a quite simple and easy assembling container is realized since the composing elements such as fan and sensors are in unit components.

Next, a practical preferred embodiments of a driving control circuit for the aromatic odorant emitting device of this invention will be hereinafter discussed in detail.

The driving control circuit for the emitting device of this invention essentially comprises a temperature detecting circuit, an illumination intensity detecting circuit, a control circuit receiving signals from the two former circuits and driving a motor, and a DC electric power source for supplying the electric power to said circuits. Its functions is as follows: it supplies a suppressing control signal to the motor to suppress the revolution speed of the motor when the room temperature exceeds the reference temperature (variable in the circuit with an adjustment), while it supplies a suppressing signal to the motor to suppress the revolution speed when the room illumination intensity decreases below the reference intensity value (variable in the circuit with an adjustment). Therefore, it suppresses the aromatic odorant emission when the room temperature is high and the illumination intensity is low, while it expedites the odorant evaporation when the room temperature is low and the illumination intensity is high, so that this device can achieve the odorant emission at a relatively constant rate throughout a year and it can suppress the uneconomical waste of the odorant when the room is dark. The terms of room temperature and illumination intensity mean those in the room, unless otherwise specified.

Now, the preferred embodiments of the driving control circuit of this aromatic odorant emitting device of this invention are hereinafter explained with reference to the accompanying drawings.

FIG. 16 is the explanatory view of the present emitting device in which an aromatic odorant container 101 contains a liquid aromatic odorant therein and the container 101 is connected with an evaporator 103 through a tubular cylinder 102, which contains a glass fiber bundle therein. The liquid aromatic odorant is absorbed to the absorbing piece 103a (shown in FIG. 17) through the glass fiber bundle by the capillary action and the piece 103a is wettably immersed. A DC power source DES may be a battery and/or a rectified power source converted from AC power, but a battery is the most convenient for easy handling, maintenance and economical sense. A control circuit C driven with said DC source DES controls the rotation of a motor M, receiving the output signals from the temperature detecting circuit TD for sensing the room temperature and an illumination intensity detecting circuit PD for sensing the room illumination intensity (hereinafter Lux). Provided at a tip end of an axis 104 of the motor M in opposite to the evaporator 103, is a fan unit 105 having a plurality of blades which blow an air onto the absorbing piece 103a to forcibly evaporate and emit the aromatic odorant therefrom.

Figure 17:
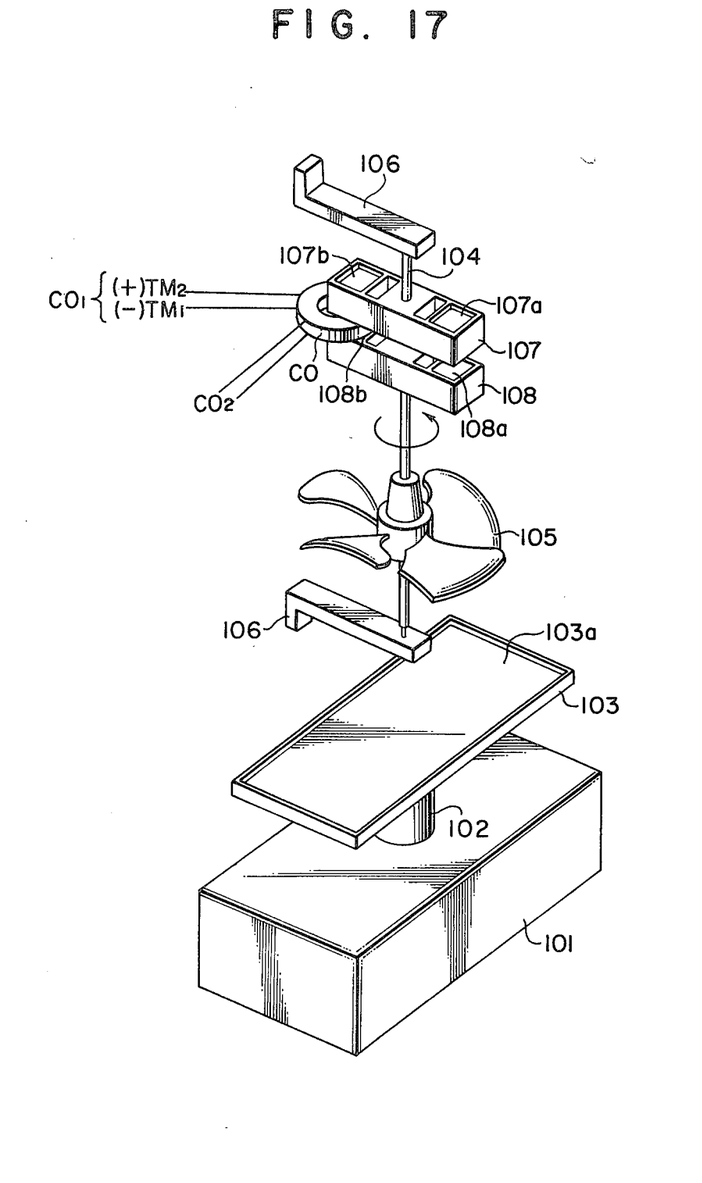
FIG. 17 is a perspective view showing one example of a motor.

FIG. 17 is a perspective view of the motor M, which is a kind of the pulse motors. Its rotary axis 104 is rotatably supported at its both ends with a pair of sleeve bearings 106, 106 and there are provided at its midway a pair of magnetic holders 107, 108 in opposite each other. At both ends of the magnet holders 107, 108, a pair of permanent magnets 107a, 107b and 108a, 108b are provided respectively. The insides of the magnets 107a, 107b are S-poles, and the outsides of them are N-poles, while the insides of the magnets 108a, 108b are N-poles and outsides are S-poles. These locations are more pertinently illustrated in FIG. 18. A coil CO is provided between the magnet holders 107 and 108 without contacting each other and the pair of magnets 107a-108a or 107b-108b are located across the center of the coil CO. The coil CO is formed with a driving coil CO1 and a controlling coil CO2 integrally wound together.

Figure 18:
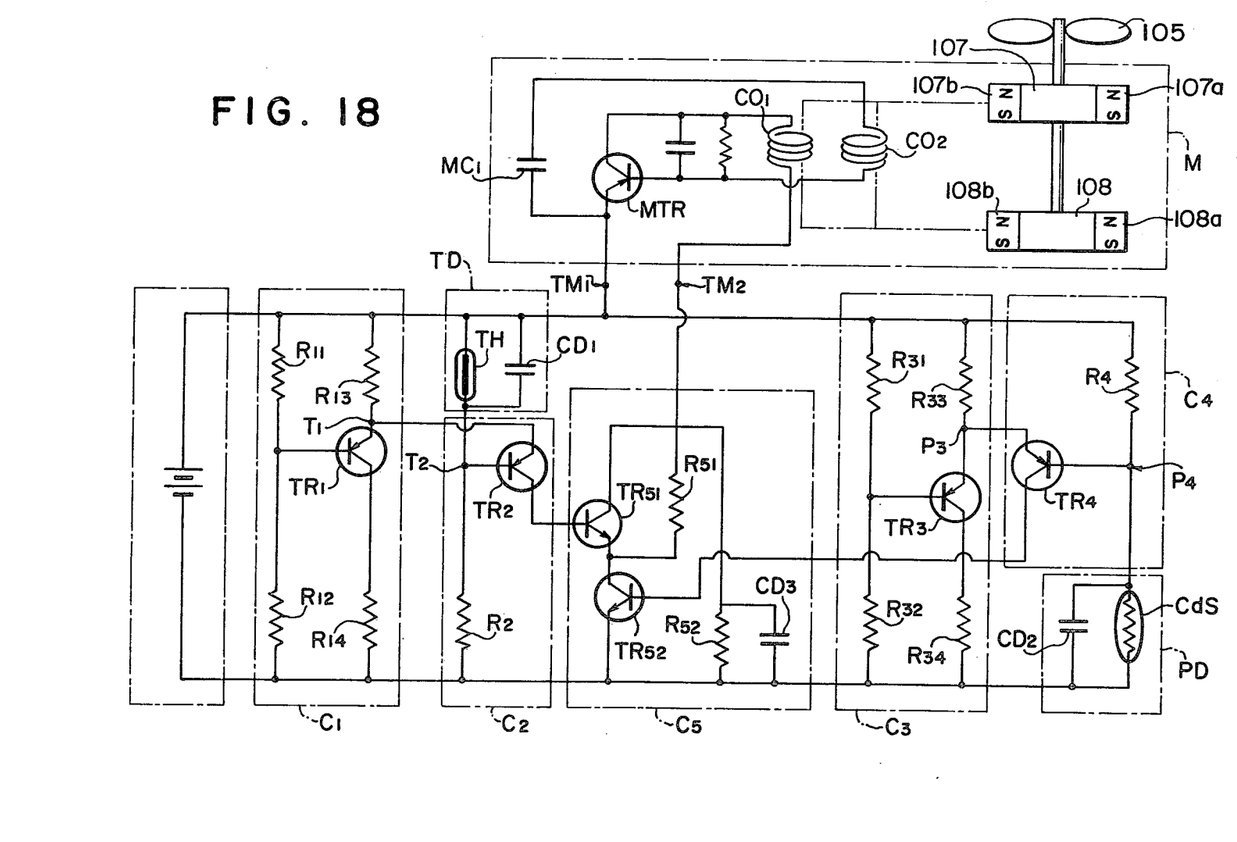
FIG. 18 is a circuit diagram for the aromatic odorant emitting device.

FIG. 18 illustrates an entire circuit arrangement for the aromatic odorant emitting device in which a control circuit C comprises five blocks composed of a temperature reference circuit C1, a temperature comparator circuit C2, an illumination intensity reference circuit C3, an illumination intensity comparator circuit C4, and a changeover circuit C5. The temperature reference circuit C1 comprises a transistor TR1 and four resistors R11, R12, R13 and R14 which determine the transistor's operative point and keep a temperature reference potential of the point T1 at a constant level. This reference level potential is arbitrarily adjustable by adjusting its resistance value, as the case may be at a desired value.

The temperature comparator circuit C2 comprises a transistor TR2 and a resistor R2. The temperature detecting circuit TD comprises a thermistor TH and a condenser CD1. As the thermistor TH and the resistor R2 are connected in series, the rise of the room temperature causes the resistance of the thermistor TH to be lower and then a rise of the potential at the point T2, and when it exceeds the temperature reference potential value at the point T1, the transistor TR2 is cut-off. When the room temperature decreases to realize that the potential level of the point T2 becomes lower than the temperature reference potential level, the transistor TR2 is switched to ON state. The condensor CD1 is a bypass condensor for noise reduction.

The illumination intensity reference circuit C3 comprises a transistor TR3 and four resistors R31, R32, R33 and R34 which determine the operative point of the transistor TR3 and this circuit C3 keeps the illumination reference potential at a constant level. This level is variable by adjusting the resistance values as the case may be at a desired value.

The illumination intensity comparator circuit C4 comprises a transistor TR4 and a resistor R4, and the illumination intensity detecting circuit PD is made up of a photosensitive element, for example CdS, and a condensor CD2.

Since the resistor R4 and CdS are connected in series, the resistance of CdS decreases with the increase of the room illumination intensity and then, when the potential of the point P4 gets lower than the illumination reference potential of the point P3, the transistor TR4 is switched to the ON state. On the contrary, the decrease of the room illumination intensity causes the transistor TR4 to be cut-off, because the potential of the point P4 becomes higher than the illumination intensity reference potential as the increase of the resistance of CdS. The condenser CD2 is a bypass condenser to reduce noises.

The changeover circuit C5 comprises transistors TR51 and TR52 for switching, and a condensor CD3 which is a bypass condensor for noise reduction. When the transistors TR2 and TR4 are set in ON state, the transistors TR51 and TR52 are switched to ON state, respectively.

The TABLE 1 shows the electric current path conducting through the motor M, the motor driving electric currents (currents between TM1-TM2), the revolving speed (r.p.m.) of the motor and the aromatic odorant emission volume with respect to the level of the temperature (Tem) and the illumination intensity (Lux).

TABLE 1

| Tem/Lux | Current path | Motor driving current | r.p.m. | Emission volume |
|---|---|---|---|---|
| High/Bright | R51 + TR52 | Medium | 650 | Medium |
| Low/Bright | TR51 + TR52 | Large | 850 | Large |
| High/Dark | R52 | Small | 450 | Small |
| Low/Dark | R52 | Small | 450 | Small |

(for example: R51 = 0.5kΩ, R52 = 1kΩ)

The motor M illustrated in FIG. 18 is a simplified view of the pulse motor shown in FIG. 17, wherein its major portion comprises a transistor MTR, a condensor MC1, a driving coil CO1 and a control coil CO2.

Figure 19:
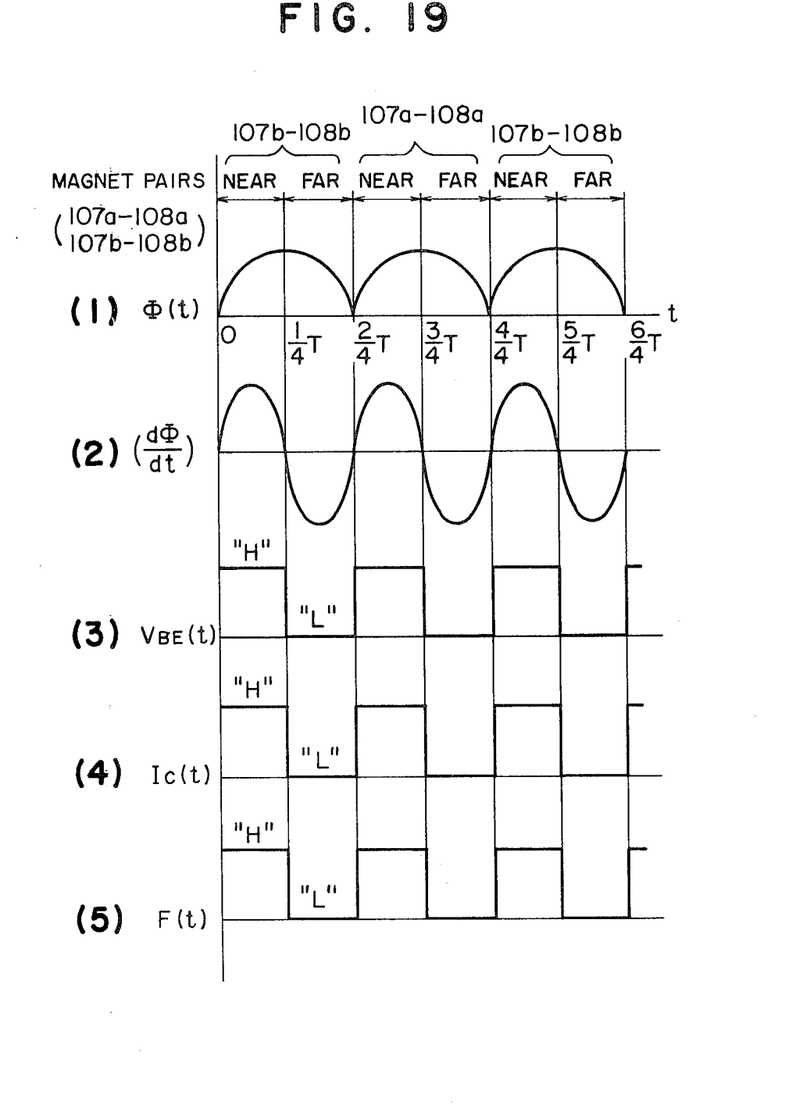
FIG. 19 is a time chart for illustrating the function of the pulse motor.

The pulse function of this motor M is hereinafter explained in detail with reference to the time chart shown in FIG. 19. Let us consider that the running time t for the flux begins from a medium point where the pair of the magnet holders 107, 108 do not move across the coil CO (See FIG. 17) and the one rotation duration is T. As the pair of the magnets 107b-108b approach the coil CO, the magnetic flux Φ (t) passing through the control coil CO2 increases and it reaches the maximum when the magnet pair 107b-108b cross the coil at t=T/4 and reaches Φ=zero (0) at t=T/2. Then, the magnet pair 107a-108a repeats the same operation and Φ (t) describes a curve as shown in (1). Consequently, an induction voltage |dΦ/dt| induced by the control coil CO2 gives a curve as shown in (2) and represents a periodic function in which the signs of the positive and negative repeat alternately. The condensor MC1 is always charged by a current coming from the point TM1 and it sets the emitter-base voltage $V_{BE}$ of the transistor MTR "H" (ON state). However, $V_{BE}$ becomes "L" (OFF state) since the |dΦ/dt| becomes an inverse voltage during the duration T/4−T/2, and this cycle is repeated thereafter as shown in (3). The collector current Ic of the transistor MTR repeats its "H" and "L" states as shown in (4), in response to a variation of the $V_{BE}$. When the Ic is in "H", the polarity of the both ends of the driving coil CO1 is generated in a direction attracting the magnet pair 107b-108b or 107a-108a and its attracting force F(t) becomes "H". To the contrary, when the Ic is in "L", the attractive force F(t) becomes "L" and keeps the rotation by its inertia for T/4 period after traversing the coil CO. In other words, as the magnet pair approaches the coil CO, the coil attracts the magnet pair, but the coil does not act for T/4 period after a passage of the magnet pairs and the magnet pair rotates by its inertia, and thereafter this periodic motion is pulsatively repeated.

The features of this pulse motor reside in the ON-OFF control of the collector current Ic and the contactless relation between the coil CO and the motor M. The former feature can suppress the power consumption to the minimum and the latter feature can decrease the accidental rate of the motor M.

Figure 20:
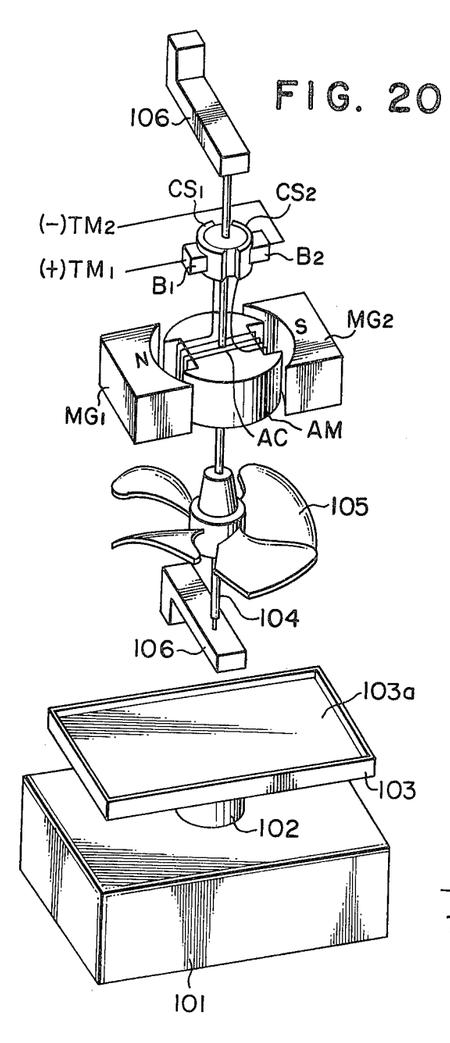
FIG. 20 is a perspective view showing a modification of the motor.

FIG. 20 illustrates a modification when a DC motor instead of the pulse motor is used for the motor M. Its rotary axis 104 is provided with a pair of commutators CS1, CS2 as well as the fan unit 105 and an armature AM wound with an armature coil AC (rotor). A pair of field magnets MG1, MG2 are contactlessly provided to surround the armature AM and a pair of brushes B1, B2 are frictionally arranged with respect to the commutators CS1, CS2. The brushes B1, B2 are connected to the points TM1, TM2 with lead wires, and the motor driving current always flows through the armature coil AC and then gives a driving power to rotate the armature AM always in one direction.

In this DC motor, by appropriately setting the contacting period of the commutators CS1, CS2 with the brushes B1, B2 namely by adjusting sizes of the commutators and the brushes, it is possible to control intermittently the driving power as well as the pulse motor.

Figure 21:
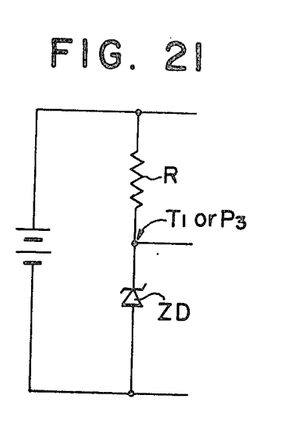
FIG. 21 is a circuit diagram showing a modification of the temperature reference and illumination intensity reference circuits.

FIG. 21 illustrates a further modification of the temperature reference circuit C1 and the illumination intensity reference circuit C3, wherein the Zener diode ZD and the resistance R enable the potentials at the points T1 and P3 to be constant.

Figure 22:
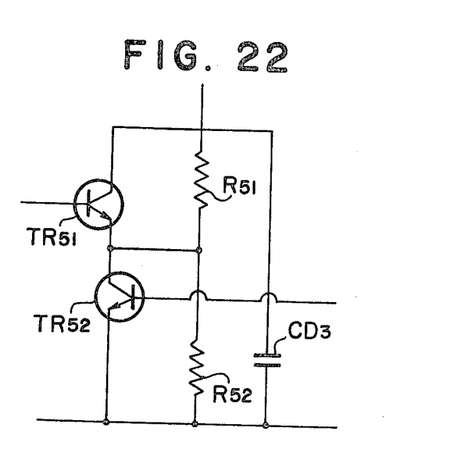
FIG. 22 is a circuit diagram showing a modification of a changeover circuit.

FIG. 22 illustrates an another modification of the changeover circuit C5, wherein a connection of the resistors R51 and R52 is changed. The TABLE 2 shows states along with the TABLE 1 in this modification.

TABLE 2

| Tem./Lux | Current path | Motor Drive current | Emission Volume Rate |
|---|---|---|---|
| High/Bright | R51 + TR52 | Medium | Medium |
| Low/Bright | TR51 + TR52 | Large | Large |
| High/Dark | R51 + R52 | Small | Small |
| Low/Dark | TR51 + R52 | Small | Small |

(for example R51 = 0.5kΩ, R52 = 1.5Ωk)

In the TABLE 2, as the R51+R52=2kΩ and R52=1.5kΩ and thus the motor driving currents in both cases are not so different each other, the resulting data are indicated as "Small."

A photodiode and a phototransistor are also equivalently available as the photosensitive element in the illumination intensity detecting circuit PD as well as CdS, as the equivalent elements to provide the same effect and function. The thermosensitive element in the temperature detecting circuit TD is not limited only to the thermistor, but any equivalent element serving the same effect and function may be employed.

As mentioned heretofore in detail, the present emitting device of this invention comprises the temperature detecting circuit, the illumination intensity detecting circuit, and the driving control circuit receiving the signals from the former two circuits to control the motor and concretely provides these circuits. Our experimental tests prove that in response to the seasonal (annual) variation of the room temperature, it can suppress the revolution speed of the motor and hence the odorant emission when the room temperature is high (for example in summer), and raise the revolution speed and hence the emission when the room temperature is low (for example in winter). Accordingly, the present device can achieve the almost constant emission throughout a year by combining the compulsory emission with the natural emission based on the room temperature.

Furthermore in response to the variation of the illumination intensity (the bright-dark fluctuation of a day), the present device can decrease the revolution speed of the motor to suppress the odorant emission when the room is dark, while increase the revolution speed of the motor to expedite the emission when the room is bright. Consequently, the device can suppress the uneconomical waste of the odorant as much as possible when the odorant is not necessary and hence can keep the life time of the odorant longer with suppressing the uneconomical waste of the electric power when unnecessary.

Thus this device provides such a new practical utility.

We claim:

1. An aromatic odorant emitting device comprising:
    (a) a first mainbody case 2 in a box shape having a plurality of openings 6f at the lower portion of its rear surface, said case being fixed onto an wall;
    (b) a second cover case 3 detachably mounted onto said first case, said second case being slightly larger than the first case and having a plurality of through slits 25 for exhaustion of an air including an aromatic odorant, at its lower portion, and having the openings 28, 30 at a center portion and a corner of an upper portion thereof;
    said first case 2 containing:
        (i) an aromatic odorant container 7 for containing the liquid aromatic odorant, to be placed on the bottom plate 5b;
        (ii) an evaporator 35 having an absorbing piece 38 which is always supplied with the liquid aromatic odorant through the glass fiber bundles 37, said aromatic odorant container being detachably mounted onto said evaporator;
        (iii) a fan unit fixed on an inside thereof being positioned in opposite to said evaporator and said opening 28 for a fan 17 of said unit;
        (iv) a photosensor 20 fixed on a portion of said first case 2, being placed in opposite to said opening 30;
        (v) a thermosensor 19 for controlling a rotational speed of said fan 17, together with said photosensor 20;
        (vi) a battery container 21 for containing at least one battery to supply its electric current to said thermosensor 19 and the photosensor 20, being detachably provided for said first case 2;
    said second case 3 having at its upper end thereof a locking mechanism 31 comprising:
        (i) a washboard-like piece 32 extending from the case 3 and having a hook 32a provided at its tip end for being engaged within an opening 9a provided on an engagement piece 9 formed on said first case 2;
        (ii) a slide lever 33 slidably attached on a backside of the washboard-like member 32, one end 33a of which extending forwardly from an opening 34 formed on a front face of said second cover case, another end of which extending at a lower side of a tip end of said washboard-like member 32, a pair of holding members 33b, 33b embracing the both sides of said forward tip end of said washboard-like member 32 being formed on said tip end of said slide lever 33.

2. An aromatic odorant emitting device according to claim 1, wherein it further comprises:
    (a) a DC power source for supplying a power;
    (b) a temperature detecting circuit for sensing a room temperature;
    (c) an illumination intensity detecting circuit for sensing a room illumination intensity;
    (d) a control circuit for receiving signals from said circuits in the (b) and (c) to drive and control a motor;
    said control circuit comprising:
        (i) a temperature reference circuit for generating a reference voltage for setting the temperature;
        (ii) a temperature comparator circuit for comparing the temperature detecting voltage sensed by said temperature detecting circuit (b) with the reference voltage generated by said temperature reference circuit (i);
        (iii) an illumination intensity reference circuit for generating the reference voltage for setting the illumination intensity;
        (iv) an illumination intensity comparator circuit for comparing the illumination detecting voltage sensed by said illumination intensity detecting circuit (c) with the reference voltage generated by said illumination intensity reference circuit (iii); and;
        (v) a change-over circuit for switching the revolution speed of the motor at a multiple stages by receiving the outputs from said both comparator circuits (ii) and (iv),
    (e) a fan unit having a plurality of fan blades, mounted on one end of the rotary axis of said motor for blowing air onto an evaporation surface of the aromatic odorant, said blown air volume being variably controlled by said combination of the circuits to variably control the evaporation rate of the aromatic odorant in response to the room temperature and the illumination intensity.

3. A device according to claim 2, wherein the motor is a pulse motor.

4. A device according to claim 3, wherein the pulse motor comprises at least a coil and a driving coil, said motor having at its rotary axis at least a permanent magnet which generates an induction voltage, which then pulsatively controls a current flowing through said driving coil.

5. A device according to claim 2, wherein the motor is a DC motor.

6. A device according to claim 2, wherein the temperature detecting circuit comprises at least a thermistor.

7. A device according to claim 2, wherein the illumination intensity detecting circuit comprises at least an element selected from a group consisting of CdS, photodiodes and phototransistors.

8. A device according to claim 2, wherein the temperature and illumination intensity detecting circuits comprise at least one selected from a group consisting of transistors and Zener diodes.

* * * * *